United States Patent [19]

Spencer

[11] 4,412,835
[45] Nov. 1, 1983

[54] STERILE DOCKING PROCESS, APPARATUS AND SYSTEM

[75] Inventor: Dudley W. C. Spencer, Wilmington, Del.

[73] Assignee: E. I. Du Pont de Nemours & Company, Wilmington, Del.

[21] Appl. No.: 395,796

[22] Filed: Jul. 6, 1982

[51] Int. Cl.³ .................. A61M 5/00; B32B 31/00
[52] U.S. Cl. .................... 604/29; 604/905; 156/296; 156/322
[58] Field of Search .............. 604/905, 29; 156/322, 156/324, 296, 304.2, 304.3, 304.5; 264/248

[56] References Cited

U.S. PATENT DOCUMENTS

| | | |
|---|---|---|
| 3,013,925 | 12/1961 | Larsen . |
| 3,035,631 | 5/1962 | Knowles . |
| 3,117,903 | 1/1964 | Hix . |
| 3,769,124 | 10/1973 | Johnson . |
| 3,834,971 | 9/1974 | Johnson . |
| 3,897,296 | 7/1975 | Waldrum . |
| 3,968,195 | 7/1976 | Bishop . |
| 4,157,723 | 6/1979 | Granzow et al. . |
| 4,209,013 | 6/1980 | Alexander et al. . |
| 4,223,675 | 9/1980 | Williams . |
| 4,242,310 | 12/1980 | Greff et al. . |
| 4,253,500 | 3/1981 | Williams . |

FOREIGN PATENT DOCUMENTS 44204  1/1982  European Pat. Off. .

*Primary Examiner*—Stephen C. Pellegrino

[57] ABSTRACT

A process, apparatus and system for making a sterile connection between two thermoplastic resin tubes is disclosed. Side sections of the adjacently placed tubes are melted by passing a heated elongated body therethrough to form a molten seal between a surface of the heated body and the adjacent side sections, thereby providing a seal between the interior and exterior of said tubes. The resulting molten tube sections are urged together as they are slid off an end of the elongated body. As the thermoplastic resin cools a sterile weld is formed.

21 Claims, 8 Drawing Figures

STERILE DOCKING PROCESS, APPARATUS AND SYSTEM

BACKGROUND OF THE INVENTION

1. Field of the Invention

This invention relates to a process, apparatus and system for forming a sterile connection (sterile docking) between two tubes.

At the present time there are a number of medical and scientific procedures which require the sterile transfer of fluids from one container to another. The only truly sterile transfer system in current use involves prejoining containers with tubes and then sterilizing the entire assembly. This is inflexible and costly since new containers cannot be added and the number of joined containers needed is often not known at the time of initial filling.

An example of the need for sterile docking is in continuous ambulatory peritoneal dialysis (CAPD). This procedure is replacing dialysis of blood outside the body in membrane diffusion cells where waste products normally removed by kidneys are washed from the blood, which is then returned to the patient. Dialysis outside of the body is a time-consuming procedure and sometimes results in damage to the blood by exposure to materials and conditions external to the body. In CAPD, the patient is required to spend time only for draining spent dialysate and replacing it with a fresh solution.

The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposes the tube ends to airborne bacteria or other contamination even though precautions are taken. No satisfactory way heretofore has existed to insure sterility in spite of the elaborate and costly precautions now employed including the use of masks, gloves, gauze strips and disinfectant solutions. Usually contamination does occur to the extent that a case of peritonitis is contracted perhaps on the average once or more a year and scar tissue from it inhibits dialysis.

Truly sterile connections could minimize the occurrence of peritonitis. Also any other treatment bags, such as for an antibiotic, bacteriostat, or other medication, could be connected as desired.

A similar need for sterile docking exists for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers, stabilizers for cell metabolism, other preservatives, or rejuvenants; or washes to remove a treating agent or other contaminant. Actually, it is not feasible to have preconnected bags for all the treatments which may be desired. Supplemental treatments such as fresh preservative cannot now be added sterilely during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood factions. The main reason for the current limited use is that heretofore any entry into a sterile blood unit exposed the blood to bacteria, thereby requiring that the blood be used within 24 hours from entry. Hence, although the viability of stored blood components can be extended by supplemental treatments, such as adding a preservative during storage, such treatments are usually not effected.

Moreover, the primary blood bag contains anticoagulant which can be sterilized only by heat (steam); thus all preconnected bags are also sterilized by wet-sterilization techniques, i.e., steam or hot water in an autoclave apparatus. These bags are made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not now used in preconnected systems.

A sterile docking means would permit one to effect whatever processing is desired without compromising sterility, limiting storage life or requiring the preconnection of a multitude of bags, all wet-sterilizable, without knowing which, if any, will be used.

REFERENCES

U.S. Pat. No. 3,013,925 discloses a method of welding two joints of thermoplastic pipe wherein the inside of each end of the joints of pipe to be welded is beveled and the ends of the pipes are heated, for example by pressing the ends of the sections of pipe against a heated plate, after which the ends of the sections are forced together so that flow of softened material is to the outside of the pipe and a weld is effected substantially without formation of a bead on the inside of the welded pipe.

U.S. Pat. No. 3,035,631 discloses a tip for welding plastic parts. The tip has a knife edge at each of two opposing ends. One end of the knife is thick whereas the other is thin. The patent states that as the thin end passes through the joint, it will induce molten plastic surfaces to flow together.

U.S. Pat. No. 3,117,903 discloses a method of joining thermoplastic pipe without forming a troublesome inside ridge at the point of weld, said method involving the immersion of the ends of pipe to be welded in inert high boiling organic liquid heated above the softening temperature of the polymer forming the pipe. Thereby, the ends of the pipe are caused to expand and flare outwardly; then the pipe is withdrawn from the bath and the ends butted together.

U.S. Pat. No. 3,897,296 discloses a method of welding two plastic surfaces together by juxtapositioning the surfaces, heating the surfaces to a temperature approaching the flash point of the plastic surfaces to liquefy the surfaces, removing a portion of the liquefied surfaces to expose unoxidized surfaces therebeneath and immediately bringing the unoxidized surfaces into abutment with one another. The patent is silent as to cutting a tube as well as forming a sterile dock.

U.S. Pat. No. 3,968,195 discloses a method for making a sterile connection between two rigid tubes the free ends of which have thermoplastic diaphragms which seal them off. The free ends of each rigid tube are aligned while being spaced slightly apart, and each thermoplastic diaphragm is opened by heating. The free ends of the rigid tubes are then brought into contact and held in position under a slight pressure while the thermoplastic material cools and solidifies, thereby creating a permanent connection. This process requires tubes which have low-melting thermoplastic diaphragms on the ends which can only be used once, i.e., another connection to the same tubing cannot be made.

U.S. Pat. No. 4,209,013 discloses an improvement in a sterile connector system for continuous peritoneal dialysis in which a dialysis solution container having a transfer port is coupled to tubing extending from a patient's peritoneal cavity. The improvement comprises a flexible housing having a first area thereof for attachment to the transfer port and a second spaced area for attachment to the patient's tubing. The attachment areas define openings for enabling the transfer port and patient's tubing to extend within the interior of the flexible housing when they are attached thereto. The flexible housing has means for receiving a sterilizing fluid therein and is operable to enable the transfer port and the patient's tubing to be sterilized within the housing and also connected to each other within the housing.

U.S. Pat. No. 4,223,675 discloses a system for producing sterile, non-autoclavable body fluid containers having autoclaved liquid therein, comprising a dry-sterilized package formed of a material which is unsuitable for being subjected to autoclave conditions, said dry-sterilized package including a sterile communication with the interior of said package; an autoclavable dispenser constructed of an autoclavable substance and containing liquid which was sterilized within the dispenser, said dispenser including a sterile connector having an initially closed sterile aperture in sterile communication with the interior of the dispenser; said package sterile connector and said dispenser sterile connector being in mating engagement with each other.

"An Aseptic Fluid Transfer System for Blood and Blood Components," B. A. Myhre et al, Transfusion, Vol. 18, No. 5, pp. 546-552, Sept.-Oct. 1978, describes a process for heat sealing two aseptic fluid transfer system (AFTS) units together. The AFTS units contain a layer of Kapton ® film (an aromatic polyimide resin which is stable at relatively high temperatures). A pair of dies, one of which is flat and one of which has a raised "H" shaped area, are brought together under a pressure of 100 psi ($6.9 \times 10^6$ dynes per square centimeter) with the AFTS units disposed between the dies. The temperature of the dies is raised to 200° C. (392° F.) over a period of 45 seconds. The dies are withdrawn and upon removal of the AFTS units from the dies, the AFTS units are heat sealed together by a seal surrounding an opening between the AFTS units. Blood bags constructed with an AFTS unit attached can thereby be joined. This system is slow and requires specially constructed units that can only be used once.

Other patents directed to sterile connection apparatuses or methods include U.S. Pat. Nos. 4,157,723, 4,242,310 and 4,253,500.

SUMMARY

The present invention relates to a process, apparatus and system for joining two sterile, closed end tubes or conduits using a hot elongated body while maintaining system sterility. The process comprising juxtaposing the tubes, forming a molten seal between a surface of a heated elongated body placed substantially perpendicularly to the axes of the tubes and an adjacent side section of each of said tubes thereby providing a seal between the interior and exterior of said tubes and moving the molten side sections of said tubes together while passing said tubes over an end of said body, thereby forming a joint between said tubes. The heated elongated body is maintained at a temperature hot enough to kill bacteria with no chance for viable airborne or surface bacteria to find their way inside either of the tubes or the joint. When the joint cools, the sterile connection or docking is complete. This invention provides a quick, inexpensive system with no special fittings permitting maximum flexibility in processing, storing and using sterile fluids.

The apparatus of the invention comprises an elongated body of substantially elliptical or circular cross section; means for heating said elongated body; a pair of spaced-apart mounting blocks adapted to receive and hold two tubes to be joined; means to provide movement between said mounting blocks and said elongated body so that, in a first position, the elongated body is substantially orthogonally between said mounting blocks and traversing where the blocks are adapted to receive said tubes and, in a second position, said elongated body and said blocks are separated; and means for urging said mounting blocks partially together as said mounting blocks and said elongated body are being separated.

BRIEF DESCRIPTION OF THE DRAWINGS

FIGS. 1-7 will be referenced to FIG. 8 as a viewpoint. In this regard, FIG. 1 is an end view.

FIG. 2 is a side view of the elongated body and the mounting blocks.

FIG. 3 is a side view of the mounting blocks, elongated body, and two tubes which are to be joined.

FIG. 4 is an end view of the mounting blocks and tubes with the hot elongated body passing through the tubes.

FIG. 5 is an end view of the mounting blocks and tubes after the hot elongated body has been removed and the tubes urged together.

FIG. 6 is a perspective view of the welded tubes.

FIG. 7 is an end view of a preferred embodiment of the mounting blocks.

DETAILED DESCRIPTION OF THE INVENTION

Figure 1:
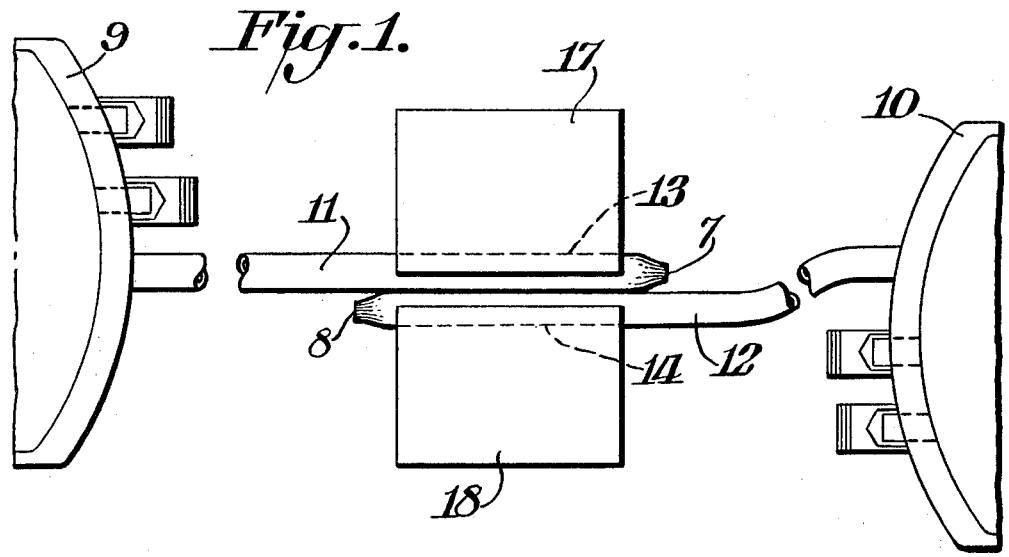
FIG. 1 is a view of the mounting blocks used to hold two tubes which are to be joined in the starting position. The particular view illustrated by the figures depends on the embodiment selected.

Referring now to FIG. 1 the sealed end 7 of thermoplastic tube 11 is inserted in slot 13, machined in block 17. The sealed end 8 of tube 12 is inserted in slot 14, machined in block 18. In FIGS. 1 and 3-6 tubes 11 and 12 are connected to blood bags 9 and 10. Alternately, one of said tubes may be connected to a dialysis bag and the other to the patient's peritoneal cavity. Also, the tube which is connected to the patient's peritoneal cavity may be connected at the other end to an empty bag in lieu of having a sealed end.

Figure 2:
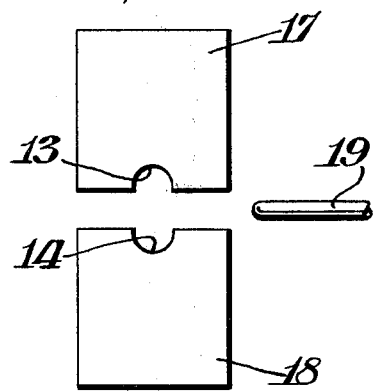
Figure 3:
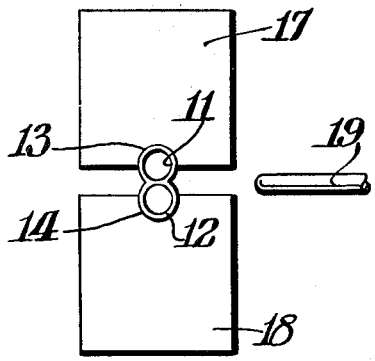

Referring now to FIG. 2, blocks 17 and 18 are shown with slots 13 and 14 which are slightly deeper than the radius of the tube so that the tubes are held in the blocks before the blocks are urged together. Referring to FIG. 3, tubes 11 and 12 are slightly pressed together by blocks 17 and 18 by means of suitable force which can be manually applied.

Figure 4:
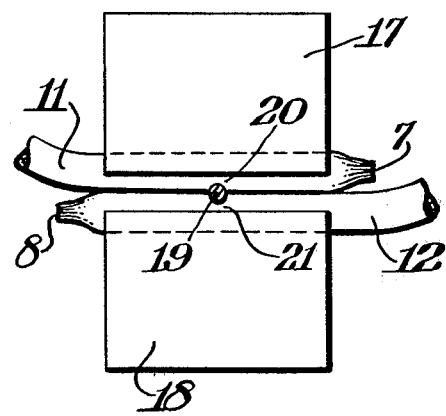

Referring now to FIG. 4, hot elongated body 19, which in this figure is a copper rod, has been moved relative to blocks 17 and 18 so that the hot elongated body has melted through tubes 11 and 12 creating molten tube interfaces 20 and 21 lying against hot elongated body 19. These molten interfaces 20 and 21 prevent exchange of air between the interior of tubes and air outside tubes 11 and 12 as well as contamination from particles suspended in the air or on the tubing or apparatus surfaces except the hot elongated body. It is to be understood that while urging the tubes together as described later herein, a momentary gap does occur and can be tolerated.

Figure 5:
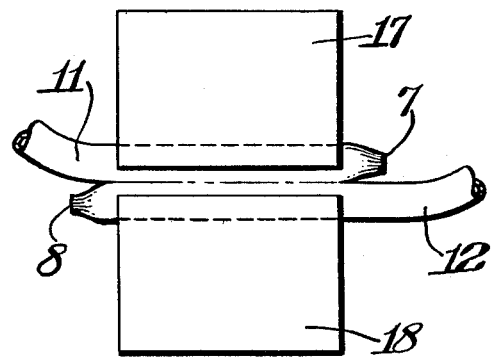
Figure 6:
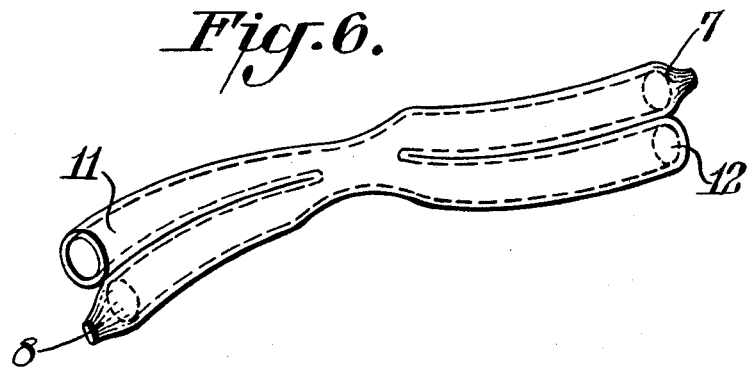

Referring now to FIG. 5, blocks 17 and 18 and hot elongated body 19 have been moved relative to each other and blocks 17 and 18 have been moved closer together to cause molten interfaces 20 and 21 to fuse and thereby join tubes 11 and 12. Referring to FIG. 6, joined tubes 11 and 12 have been removed from mounting blocks 17 and 18. The tubes show a depression opposite the place where the joint was made.

Figure 7:
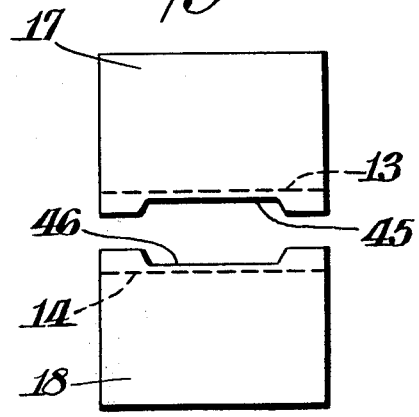

Referring to FIG. 7, a preferred embodiment of blocks 17 and 18 is shown wherein slots 13 and 14 extend deeper than the tube radius only at the extremities of the blocks, thereby providing spaces 45 and 46 which give clearance for the hot elongated body when additional room is necessary.

Figure 8:
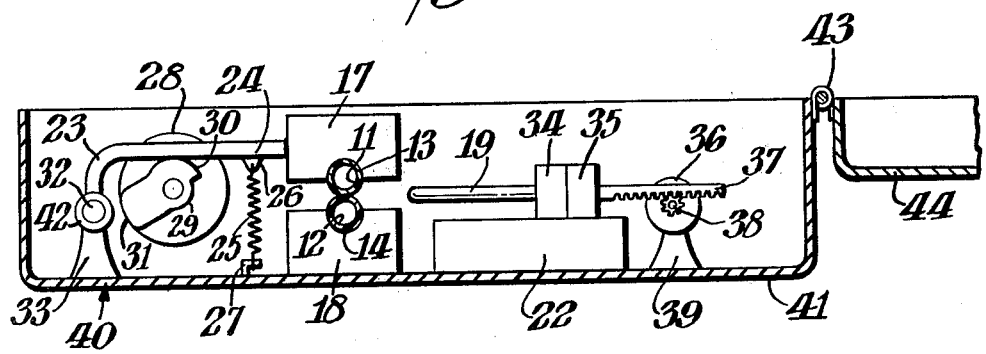
FIG. 8 is a side view of mounting blocks fixedly arranged in a housing, shown in cross-section for clarity, along with the means for operating the elongated body.

FIG. 8 illustrates another embodiment for carrying out the present invention. In this embodiment tubes 11 and 12 are placed in slots 13 and 14, machined in blocks 17 and 18, respectively. Block 17 is attached to arm 23 which pivots about bolt 32 via collar 42. Bolt 32 is fixedly attached to pedestal 33 which in turn is mounted on the base 40 of housing 41. The tubes 11 and 12 are slightly pressed together by means of spring 25 pulling on arm 23. Spring 25 is attached to arm 23 by being hooked thereto at hole 24 in flange 26 and is attached to base 40 by hook 27. Cam 28 imparts three positions to block 17. In the first position, determined by step 31, the blocks are wide open. In the second position, determined by step 30, block 17 is lowered by spring 25 to press tubes 11 and 12 slightly together. In the third position, determined by step 29, block 17 is lowered further to seal the two tubes together. The cam can be manually operated or driven by a DC motor.

The hot elongated body 19 is mounted in cartridge heater 34 which in turn is fixedly attached to block 35. The hot elongated body 19 is a copper rod with a rounded end. Block 35 rides on block 22 and is moved by action of gear 38 on toothed arm 37 extending from block 35. Gear 38 is driven by DC motor 36. A microswitch (not shown) serves to reverse the advance of hot elongated body 19. Blocks 18 and 22 are fixedly arranged in a base portion 40 of housing 41. Motor 36 is fixedly attached to pedestal 39 which is mounted on base portion 40 of housing 41. The upper portion 44 of housing 41 is optional and serves to close the operation from the outside environment. The two portions of housing 41 are attached by hinge 43.

In operation of this embodiment, after tubes 11 and 12 are inserted in slots 13 and 14, cam 28 originally positioned at step 31 is moved to step 30, and the cartridge heater is activated. Motor 36 is activated and hot elongated body 19 advances on block 22 toward the tubes. Hot elongated body 19 melts through the adjacent walls of tubes 11 and 12. Continued advancement of body 19 via block 35 activates a microswitch (not shown) which causes block 35 to reverse its course. As hot elongated body 19 is separated from the tubes, molten interfaces 20 and 21 (FIG. 4) are wiped across body 19 and are pressed together by movement of cam 28 to step 29 and thereby enabling further urging from the spring 25. Step 29 also limits the extent to which the blocks can be urged together thereby assuring the proper amount of compression. When block 35 returns to its starting position, cartridge heater 34 and motor 36 are deactivated. The joined tubes can be removed after about five seconds delay for the joint to cool.

The elongated body used in the present invention can be made of any material having sufficient heat capacity and heat conductivity to heat adequately and to melt the tubes. Suitable materials include steel, silver, titanium and copper. Preferably, the elongated body is made of copper. It can be heated by electrical resistance, induction heating, radiation-convection in a small tube furnace, or by internal heat transfer fluid connected to a hot fluid source. The elongated body is free of side corners and has an elliptical or circular cross section with elliptical being preferred. The end of the elongated body which passes through the tubes can be round or flat but round is preferred. The cross section of the elongated body can have an axis, positioned transverse to the tubes, of from about at least 50% greater than the sum of the wall thickness of each tube to about 100% of the outer diameter of the tubes or 100% of the outer diameter of the smaller of the tubes to be joined if the tubes are of different sizes. The cross-sectional dimensions of the elongated body should be such that the connecting pore created in the tubes will not unduly restrict the flow of fluid in tubes.

Currently-used blood and dialysis bags and tubes are made of plasticized polyvinyl chloride for flexibility, strength and steam sterilizing. Generally, for these plasticized polyvinyl chloride tubes, the elongated body will be heated to a temperature of from about 500° F. (260° C.) to 750° F. (399° C.) which is also suitable for most other thermoplastic tubing. The elongated body preferably is at a temperature high enough (1) to kill rapidly (less than one second) any bacteria or bacterial spores on the outside surface of the tubes and (2) to melt rapidly the thermoplastic resin from which the tubes are formed. The tubes are heat-sealed closed at their ends or connected to a bag. The tubes and whatever bag or bags they are connected to will have been sterilized. Below about 500° F. (260° C.) bacterial and bacterial spores are not rapidly killed by the heat from the elongated body. Above about 750° F. (399° C.) most polymers such as plasticized polyvinyl chloride or polyolefins such as polypropylene or polyethylene begin to become too liquid to maintain a seal with the elongated body. About 600° F. (316° C.) is the preferred temperature for use with conventional plasticized polyvinyl chloride blood bag tubing. Another upper limit is the temperature where the resin from which the tube is made begins to degrade in the time it is exposed to the heated elongated body (about 2 seconds). For plasticized polyvinyl chloride and polyolefins the upper limit is about 300° F. (149° C.) above the melting point of the thermoplastic resin from which the tube is made.

The elongated body should be advanced into the tubes at a rate such that the polymer from which the tubes are fabricated melts up against the elonggated body and there should be no mechanical rupturing of unmolten polymer or significant visible deformation of the tubes. Excessive heating times are to be avoided in order to minimize excess melting or degradation of the polymer. For conventional 165 mil (4.2 mm) outside diameter, 10 mils (0.25 mm) thick wall plasticized polyvinyl chloride blood bag tubing, a time of 0.5 to 1.5 seconds for melting through the walls of the two tubes has been found to be most satisfactory. The speed of withdrawal of the elongated body is important to minimize degradation and excess melting and 0.1 to 0.5 seconds should be satisfactory. Completion of the joint occurs after the elongated body has been fully removed and should be effected within about 0.5 seconds or less after such removal. After removal of the hot elongated body, cooling of the tubes takes about five seconds and the tubes are then removed from the blocks.

The mounting blocks are made of heat conductive metal and serve as heat sinks to assist rapid cooling of the joint. It is necessary that the tubes be urged toward each other as the hot elongated body is removed. The tube slot in each mounting block is slightly deeper than the radius of the tube it holds. The space between the blocks and the slots in them should be such that the two tubes at least nearly touch each other; preferably, the space is such that the two tubes just touch each other. The space between blocks adjacent the tubes should be at least about ⅓ greater than the vertical dimension of the hot elongated body. Otherwise, the space between the blocks is not important. The mounting blocks, the slots in said blocks and cam 28 (FIG. 8) are dimensioned appropriately for the particular size of tubes being connected so that the amount of compression of the tubes is suitable, i.e., compression that provides completion of a seal with melted interfaces compressed together from at least about 0.51 mm (20 mils) to about 1.5 mm (60 mils) at the tube areas opposing the molten interfaces.

The tubing used should be formed of a thermoplastic resin which melts at least 50° F. below the temperature at which it begins to degrade in the time exposed to heat in the process of the present invention. The tubes to be connected are preferably of the same diameter but can have different diameters so long as the big tube has sufficient flexibility to wrap around the smaller tube to make a seal. When the tubes are of different diameters the hole made in the two tubes by the hot elongated body is preferably as large as the inside diameter of the smaller tube. The tubes to be joined can be made of the same material or can be made of compatible resins. "Compatible resins" as used herein means that the melting points of the two materials are close enough so that at the operating temperature both form thick, viscous melts which will flow together to form a single melt phase without polymer degradation or formation of thermal or other chemical reaction products which would weaken or otherwise interfere with formation of the single melt phase and its subsequent cooling and solidification to a strong joint. For example, polyethylene is compatible with polyethylene copolymers and polypropylene.

In order to obtain a secure dock, tubes to be joined must not contain more liquid than a thin film on the walls at or near the locations where they are to be melted or joined. Generally the length of tubing which is empty of liquid need not be more than about 0.5 to 1 inch (13-25 mm). Normally, in joining the tubes, if either tube is connected to a bag filled with liquid, the tube is clamped shut below where the tube is to be joined. After the joint has been made, an unwanted bag, such as one containing spent liquid, is removed by sealing its tube with a Hemitron ® device somewhat below the joint and then cutting the tube below the seal.

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment of the invention the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected and the patient's tube can be joined to a sterile sealed-end tube. It also eliminates the need for the present laborious procedure used to achieve sterility.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port, e.g., having a protective covering and a septum inside the port. The bags can also be connected by joining the blood collection tube of the donor bag to the connection tube of the transfer bag. In another embodiment, the blood collection tube and the connection tube of the transfer bag both have a sealed distal end.

In the preferred embodiment for both the blood bag system and the CAPD system, the donor bag and dialysis bag have, specifically for sterile connection, an additional tube (pigtail) which is connector-free and has a sealed distal end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like. This modified bag is further described in copending U.S. application Ser. No. 267,291, the relevant disclosure of which is incorporated herein by reference. The tube is equipped with means, such as a clamp, to prevent undesired flow of liquid into said tube.

In the present system for the sterile connection of blood bags, the need to pre-assemble bags into a system is eliminated. It is to be understood that the expression "blood bag" as used herein refers collectively to either the donor (primary) bag or the satellite bag. With the present invention satellite bags can be sterilely connected to a donor bag as the need arises. The donor bag can be made from a wet-sterilizable material, such as polyvinyl chloride whereas the satellite bags do not have to be wet-sterilizable but can be made of material which can be sterilized only by dry-sterilization means, such as irradiation or ethylene oxide treatment. For example, the satellite bag can be constructed from $O_2$ permeable polyethylene which would increase platelet viability. Alternatively, the satellite bag can be made from a polyethylene copolymer, a polyethylene laminate, polypropylene, or any other material which is compatible with the material from which the donor bag is constructed. The satellite bag can be made from material which is incompatible with the material from which the donor bag is constructed so long as the tubes to be connected are made of compatible materials. For instance, the donor bag and its tubing can be made from polyvinyl chloride whereas the satellite bag can be made from polyethylene but its tubing made from polyvinyl chloride and solvent welded to the satellite bag. Techniques for solvent welding are well known in the art. Supplemental treatments can be sterilely added and washing to remove treating agents can be sterilely effected. Some practitioners believe hepatitis risks can be reduced by washing red cells without previous freezing.

The sterile docking apparatus of the invention can also be used to provide a system for producing sterile, non-autoclavable body fluid containers having wet-sterilized (autoclaved) liquid therein. The system is similar to that described in U.S. Pat. No. 4,223,675; however, the present apparatus eliminates the need to have special connectors attached to the tubing.

With the present invention a dry-sterilized package can be formed from a synthetic resin material which is unsuitable for being subjected to wet-sterilization conditions but is particularly suitable for prolonged storage of body fluids. The autoclavable liquid is placed in an autoclavable dispenser equipped with an access tube which can then be heat-sealed closed. The dispenser package and liquid are then wet-sterilized in an autoclave. The dispenser package is next sterilely connected to a dry-sterilized container by using the apparatus and process of the invention. The dry-sterilized container can be equipped with a connector-free tube having a sealed distal end, said tube being specifically for sterile connection. After the sterile connection is made the autoclaved liquid is transferred to the dry-sterilized container which is non-autoclavable. If desired, the two containers can be separated by heat sealing the connecting tube while moving the containers apart so that each container is left with a connector-free tube having a sealed distal end. The autoclavable liquid can be an anticoagulant and the autoclavable dispenser package can be constructed from polyvinyl chloride. The non-autoclavable container can be a blood bag constructed from materials such as those previously described herein.

The process of the invention for joining two thermoplastic tubes together comprises juxtaposing said tubes, forming a molten seal between a surface of a heated elongated body placed substantially perpendicularly to the axes of said tubes and an adjacent side section of each of said tubes thereby providing a seal between the interior and exterior of said tubes and moving the resulting molten side sections of said tubes together to form a joint between said tubes while maintaining said seal.

The process of the invention can be carried out using the herein-described specific embodiment of the apparatus of the invention but is not limited thereto. The conditions of operations are those previously set forth herein. Subsequent docks to the same tube can be effected by heat sealing the tube with a Hemitron ® device immediately below the joint on the bag side of the tube; cutting off, at the seal just made, the unwanted joint and the bag connected thereby while providing a sealed end on the desired tube; and then connecting the new tube as herein described.

I claim:

1. A process of joining first and second thermoplastic tubes together comprising juxtaposing said tubes, forming a molten seal between a surface of a heated elongated body placed substantially perpendicularly to the axes of said tubes and an adjacent side section of each of said tubes thereby providing a seal between the interior and exterior of said tubes and moving the molten side sections of said tubes together while passing said tubes over an end of said body, thereby forming a joint between said tubes.

2. A process of forming a sterile connection between a first tube and a second tube, both formed of thermoplastic resin, comprising mounting said tubes in a pair of spaced-apart mounting means which hold said tubes in a contiguous, substantially parallel position; urging a hot elongated body having substantially elliptical or circular cross section through opposing side sections of said tubes substantially perpendicularly to the axes of said tubes at a rate such that the thermoplastic resin from which said tubes are formed and which is in contact with said body becomes molten, thereby forming a molten interface between the surface of said body and each of said tubes and providing a seal between the interior and exterior of said tubes; passing said tubes over an end of said body while urging the molten sections of said tubes together; and cooling the thusly joined molten interfaces whereby a sterile connection is formed between said tubes.

3. A process according to claim 2 wherein the hot elongated body is maintained at a temperature above about 260° C.

4. A process according to claim 3 wherein the hot elongated body is maintained at a temperature below the temperature where the thermoplastic resin from which the tubes are made begins to degrade in the time used.

5. A process according to claim 4 wherein the mounting means holding the tubes are a pair of blocks having slots therein which hold said tubes.

6. An apparatus for forming a sterile connection comprising
an elongated body of substantially elliptical or circular cross section;
means for heating said elongated body;
a pair of spaced-apart mounting blocks positioned in facing relationship and adapted to receive and hold two tubes to be joined;
means to provide movement between said mounting blocks and said elongated body such that the elongated body is positioned substantially orthogonally between said mounting blocks and traversing where the blocks are adapted to receive said tubes;
means to separate said mounting blocks and said elongated body; and means for urging said mounting blocks partially together as said mounting blocks and said elongated body are being separated.

7. An apparatus for forming a sterile connection comprising
an elongated body of substantially elliptical or circular cross section;
means for heating said elongated body;
a pair of spaced-apart mounting blocks positioned in facing relationship and adapted to receive and hold two tubes to be joined;
means to provide movement between said mounting blocks and said elongated body so that first and second positions are obtained, the elongated body being substantially orthogonally between said mounting blocks and traversing where the blocks are adapted to receive said tubes in said first position and said elongated body being separated from said mounting blocks in said second position; and
means for urging said mounting blocks partially together as said mounting blocks and said elongated body are being separated.

8. An apparatus according to claim 7 wherein the elongated body is made of copper.

9. A sterile connection system for continuous ambulatory peritoneal dialysis in which a dialysis solution container with a transfer port that includes a segment of tubing is coupled to a tube extending from a patient's peritoneal cavity, wherein the improvement comprises an elongated body of substantially elliptical or circular cross section; means for heating said elongated body; a pair of spaced-apart mounting blocks positioned in facing relationship and adapted to receive and hold the transfer port tube and the patient's tube; means to provide movement between said blocks and said elongated body such that, in a first position, said elongated body is positioned substantially orthogonally between said blocks and traversing where the blocks are adapted to receive said tubes and, in a second position, said elongated body and said blocks are separated; and means for urging said blocks partially together as said mounting blocks and said elongated body are being separated.

10. A sterile connection system according to claim 9 wherein the patient's tube is connector-free and has a sealed distal end.

11. A sterile connection system according to claim 10 wherein the transfer port tube is connector-free, has a sealed distal end, and is the same diameter as that of the patient's tube.

12. A sterile connection system for joining two blood bags, each bag having a tube which can be used for connection and sterile connection being made by joining said tubes, wherein the improvement comprises an elongated body of substantially elliptical or circular cross section, means for heating said elongated body; a pair of spaced-apart mounting blocks positioned in facing relationship and adapted to receive and hold the tubes to be joined; means to provide movement between said blocks and said elongated body such that, in a first position, said elongated body is positioned substantially orthogonally between said blocks and traversing where the blocks are adapted to receive said tubes and, in a second position, said elongated body and said blocks are separated; and means for urging said blocks partially together as said mounting blocks and said elongated body are being separated.

13. A sterile connection system according to claim 12 wherein one of the bags is a donor bag and its blood collection tube is one of the tubes to be joined.

14. A sterile connection system according to claim 13 wherein the two tubes to be joined are of the same diameter.

15. A sterile connection system according to claim 14 wherein the blood collection tube has a sealed distal end.

16. A sterile connection system according to claim 15 wherein the second bag is a transfer bag having a transfer port with a transfer tube and the transfer tube is the other tube to be joined.

17. A sterile connection system according to claim 16 wherein the transfer tube has a sealed distal end.

18. A sterile connection system according to claim 12 wherein one of the bags is a donor bag having, in addition to its blood collection tube, a connector-free tube to be used specifically for sterile connection, said tube having a sealed distal end.

19. A sterile connection system according to claim 18 wherein the donor bag is steam sterilizable and the other bag is a transfer bag made from material which is dry sterilizable only.

20. A sterile connection system according to claim 19 wherein the transfer bag has a connector-free tube having a sealed distal end.

21. A sterile connection system according to claim 20 wherein the two tubes to be connected are of the same diameter.

* * * * *